United States Patent
Lu et al.

(10) Patent No.: US 10,596,395 B2
(45) Date of Patent: Mar. 24, 2020

(54) FOCUSED ULTRASOUND SPLIT-FOCI CONTROL USING SPHERICAL-CONFOCAL-SPLIT ARRAY WITH DUAL FREQUENCY OF FUNDAMENTAL AND HARMONIC SUPERIMPOSITION

(71) Applicant: XI'AN JIAOTONG UNIVERSITY, Xi'an, Shaanxi (CN)

(72) Inventors: Mingzhu Lu, Shaanxi (CN); Rui Wang, Shaanxi (CN); Linglu Zhang, Shaanxi (CN); Mingxi Wan, Shaanxi (CN); Yubo Guan, Shaanxi (CN); Tengju Dong, Shaanxi (CN)

(73) Assignee: XI'AN JIAOTONG UNIVERSITY, Xi'an, Shaanxi (CN)

( * ) Notice: Subject to any disclaimer, the term of this patent is extended or adjusted under 35 U.S.C. 154(b) by 565 days.

(21) Appl. No.: 15/311,190

(22) PCT Filed: Jul. 21, 2015

(86) PCT No.: PCT/CN2015/084678
§ 371 (c)(1),
(2) Date: Nov. 15, 2016

(87) PCT Pub. No.: WO2016/134581
PCT Pub. Date: Sep. 1, 2016

(65) Prior Publication Data
US 2017/0080259 A1    Mar. 23, 2017

(30) Foreign Application Priority Data
Feb. 28, 2015 (CN) .......................... 2015 1 0091561

(51) Int. Cl.
| | | |
|---|---|---|
| *A61B 18/02* | (2006.01) | |
| *A61N 7/02* | (2006.01) | |
| *A61N 7/00* | (2006.01) | |

(52) U.S. Cl.
CPC .......... *A61N 7/022* (2013.01); *A61B 18/0206* (2013.01); *A61N 2007/0073* (2013.01); *A61N 2007/0082* (2013.01)

(58) Field of Classification Search
CPC ............ A61N 7/022; A61N 2007/0082; A61N 2007/0073; A61B 18/0206
(Continued)

(56) References Cited

U.S. PATENT DOCUMENTS

| 5,523,058 A * | 6/1996 | Umemura ................. A61N 7/02 134/1 |
| 5,601,526 A * | 2/1997 | Chapelon ................. A61N 7/02 601/2 |

(Continued)

*Primary Examiner* — Ronald Hupczey, Jr.
*Assistant Examiner* — Christine A Dedoulis

(57) ABSTRACT

A spherical-confocal-split array with dual frequency of fundamental and harmonic superimposition includes: array elements which are spherically confocal, whose quantity is an even number, wherein a half of the array elements operate with a lower frequency, and the other half of the array elements operate with a higher frequency; both the lower frequency and the higher frequency are MHz high-frequencies; each of the array elements corresponds to a frequency drive; array element beams don't superimpose outside the focal region; each of the array elements is connected to a channel amplifier (3) through corresponding impedance matching (2); and a multi-channel waveform controller (4) is connected to the channel amplifier (3) for controlling amplitudes and phases of all channels. The dual-frequency spherical sectorial split array is able to generate split multi- (Continued)

foci of the focal plane with the dual frequencies; and control strong interference of transient cavitation clouds at the adjacent foci.

2 Claims, 10 Drawing Sheets

(58) Field of Classification Search
USPC .......................................................... 606/27
See application file for complete search history.

(56) References Cited

U.S. PATENT DOCUMENTS

| | | | |
|---|---|---|---|
| 9,936,969 B2* | 4/2018 | Vincenot | G10K 11/32 |
| 2009/0281463 A1* | 11/2009 | Chapelon | A61N 7/02 |
| | | | 601/2 |
| 2012/0123302 A1* | 5/2012 | Liu | A61N 7/00 |
| | | | 601/2 |
| 2013/0116561 A1* | 5/2013 | Rothberg | A61B 8/4254 |
| | | | 600/438 |
| 2016/0184616 A1* | 6/2016 | Cain | A61N 7/00 |
| | | | 601/2 |

* cited by examiner

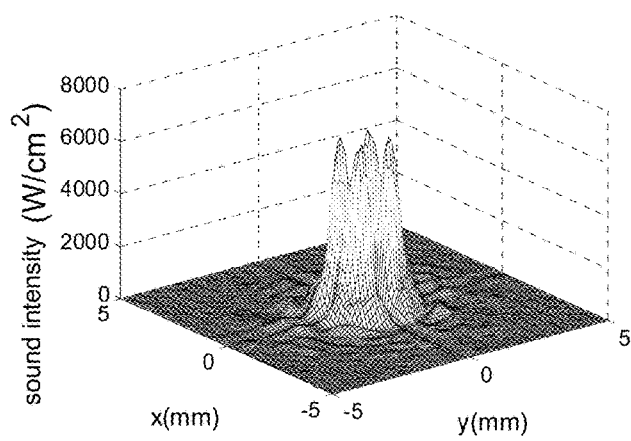
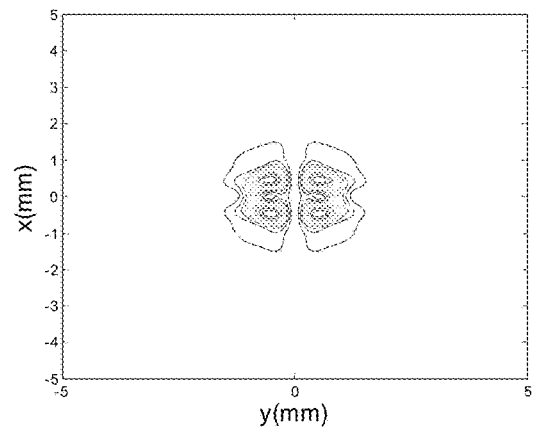
Fig. 7(a)　　　　　　Fig. 7(b)
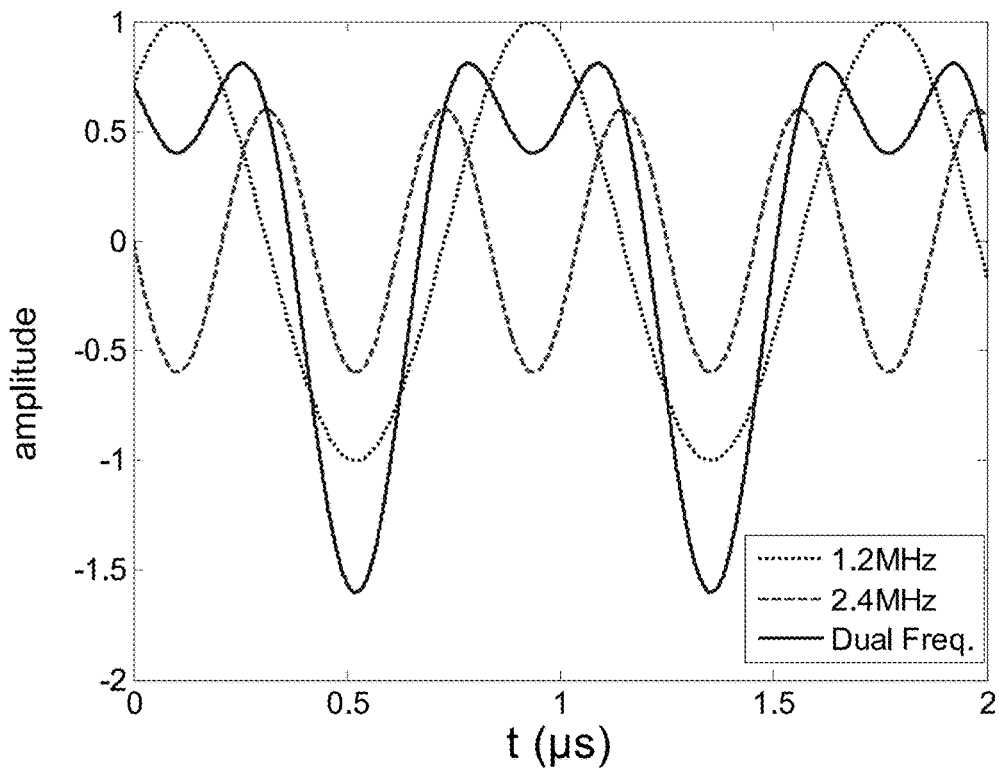
Fig. 8

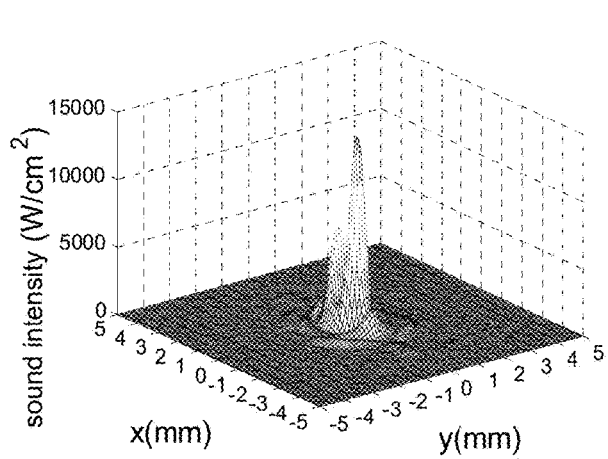
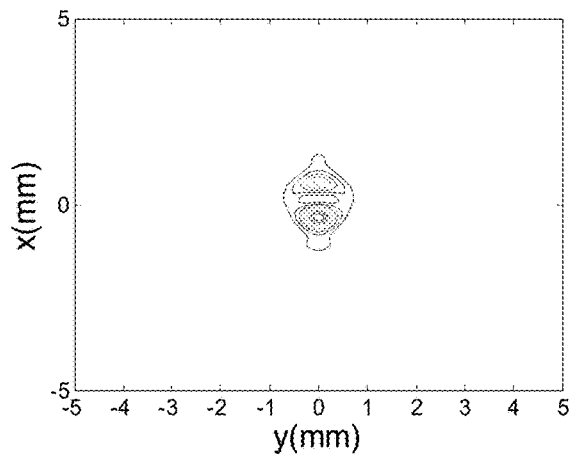
Fig. 9(a)  Fig. 9(b)
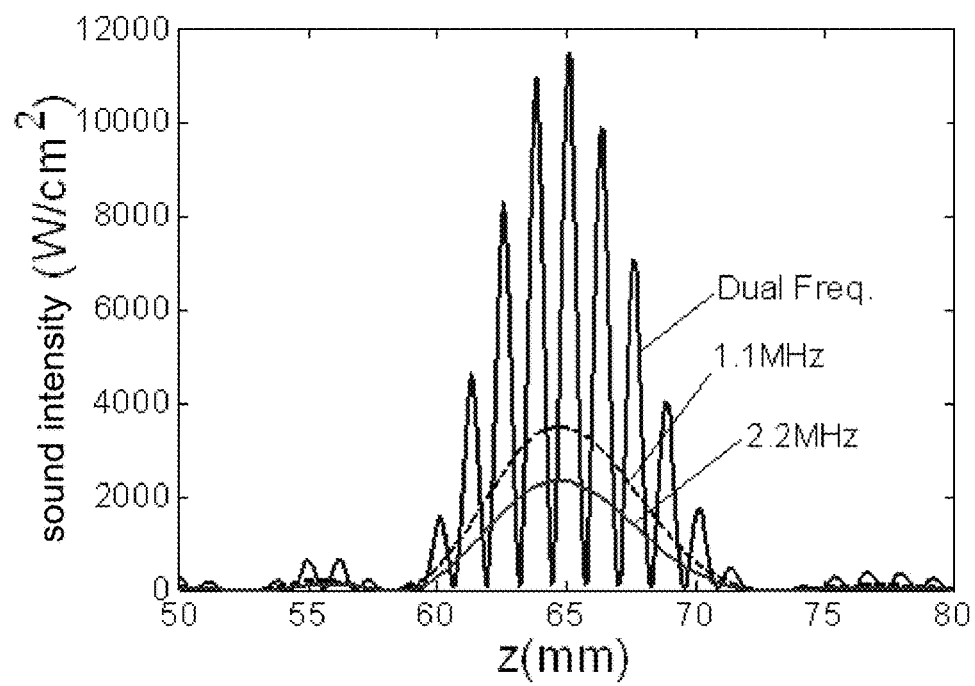
Fig. 10

FOCUSED ULTRASOUND SPLIT-FOCI CONTROL USING SPHERICAL-CONFOCAL-SPLIT ARRAY WITH DUAL FREQUENCY OF FUNDAMENTAL AND HARMONIC SUPERIMPOSITION

CROSS REFERENCE OF RELATED APPLICATION

This is a U.S. National Stage under 35 U.S.C 371 of the International Application PCT/CN2015/084678, filed Jul. 21, 2015, which claims priority under 35 U.S.C. 119(a-d) to CN 201510091561.1, filed Feb. 28, 2015.

BACKGROUND OF THE PRESENT INVENTION

Field of Invention

The present invention relates to technical field of medicine focused ultrasound, and more particularly to focused ultrasound split-foci control using spherical-confocal-split array with dual frequency of fundamental and harmonic superimposition.

Description of Related Arts

Focused ultrasound surgery (FUS) focuses ultrasound energy on the body deep target tissue, so as to precisely choose injured target tissue without injuring adjacent normal tissues. Conventionally, FUS is mainly used for non-invasive treatment of tumors and deep tissues. And high intensity focused ultrasound (HIFU) comprises two treatments such as thermal ablation using ultrasound thermal mechanism and histotripsy using local mechanical force of cavitation.

Conventionally, HIFU treatment mainly depends on thermal mechanism, wherein effectively using cavitation thermal mechanism is still the subject of conventional researches, and HIFU treatment generally adapts a single-frequency (0.5 MHz-10 MHz). Due to a larger tumor size generally up to several $cm^3$ and HIFU single-focus only a few $mm^3$ which leads to an ultrasonic irradiation with size a few $mm^3$ for one time, treating a tumor of a few $cm^3$ requires an exposure time of more than hundreds of times (a few hours), causing a long treatment period. So how to improve the treatment efficiency and shorten the treatment period is the key problem to be solved. There are spatial solving method which expands the size of the focal region by using phased array to produce multi-foci simultaneously, and temporal one which uses cavitation synergistic mechanism. About cavitation synergism, a previous method used dual-frequency, i.e. a lower kHz frequency and a higher MHz frequency, wherein a cavitation threshold of the lower kHz frequency is lower for easily generating cavitation, and the higher MHz frequency provides higher heat efficiency.

In order to obtain a large sound intensity gain, a spherical cap (concave spherical surface) with a geometric shape is generally used as an appearance of a phased array therapy transducer, wherein array elements are arranged on the spherical surface. The array elements may be annular, circular, rectangular, sectorial, sector-vortical, etc., wherein the annular, rectangular, sectorial and sector-vortical forms are tightly arranged manner. Conventionally, probe size of the therapy transducer is generally large with a diameter approximately 3-20 cm, so as to obtain a large sound intensity gain. However, the phased array transducer must be small to produce no grating lobes during scanning a certain area, so the number of the array elements tends to be larger than 128, such as 128, 256, 1024 or 2048 array elements, and the number of driving channels will also be more than 128, leading to complex structure and control of a driver. Conventional HIFU phased array technologies are all driven by a single-frequency. U.S. Pat. No. 4,865,042 of Umemura, ultrasonic irradiation system, was an early disclosure of a spherical cap phased array transducer in 1989, which discloses a spherical cap phased array transducer, i.e. spherically annular phased array and a spherically vortical phased array, wherein by controlling a driving mode, multi-foci which are annular distributed on a focal plane are provided, while the single-frequency in the driving method is only used for phase control, and amplitude of each element remains the same. U.S. Pat. No. 6,613,004B1 of Israel InSightec-TxSonics, Ltd., system and method for creating longer necrosed volumes using a phased array focused ultrasound, together with a corresponding Chinese patent CN01813606.0, system and method of focused ultrasound system with phased array to increase volume of necrosis, discloses alternating two focus modes, full array equal amplitude and apodization, for spherically vortical phased array, which increases treatment volume of tissue damage during focused ultrasound surgery with phased array, so as to overcome pre-focus area overheating caused by tissue damage volume generated by apodization. U.S. Pat. No. 6,503,171B1 of the same company, system and method for controlling distribution of acoustic energy around a focus using a focused ultrasound system, uses a sectorial array which only controls the phase for producing annular multi-foci on the focal plane. Phased array inventions of China are as follows. Chinese application CN 2007100451792 of Shanghai Jiaotong University, phased array focused ultrasound method for forming a multi-mode thermal field, and Chinese patent ZL200610023637.8, phased array focused ultrasound method for forming a large focal region, both disclose a phased array with 108 circular array elements mounted on a spherical cap surface, which adapt a rotating alternative focal method for uniformly heating and increasing a thermal field therapy volume, and focal control is optimized by matrix pseudo-inverse and the cost function of thermal field. In 2006, Chinese application CN 2005101111028.3 of CHEN, Yazhu et al., large focal region phased focusing system for heating deep tumor lesions, disclosed a channel phase and amplitude control method of a phased array system and system configuration thereof. Chinese patent ZL200610114747.5 of Chinese Academy of Sciences, phased focused ultrasound source device, discloses a phased array element structure where circular array elements are mounted in the spherical cap. Chinese patent ZL200510096069.x of Xi'an Jiaotong University, sound field focus mode drive control method of spherical phased array focused ultrasound transducer, provides three-dimensional multi-focus control with a mode control method optimized by combination of spherically rectangular array element phased array sound field calculation and multi-focus genetic algorithm; and another Chinese patent ZL200910024284.7, focused ultrasound therapeutic composition array element phased array and multi-focus shear wave imaging system, uses a spherically rectangular array element combination structure, wherein driving channels are reduced while an total array element area is kept the same, while both the focus area with multi-foci and no grating lobes, as well as multi-focus scanning range are expanded.

Conventionally, the Chinese application CN201410456237.0, histotripsy and thermal coagulation device and method based on dual-frequency confocal ultrasound time-sharing excitations, uses dual-frequency focused ultrasound, but in a time-sharing mode, which is mainly for synergies of phase transition droplets. Chinese patent publication CN 102793980A, dual-frequency focused ultrasound system, mainly discloses a system with a small difference frequency which is less than 1% of the base frequency. An article titled "Vibro-acoustic tissue mammography" IEEE Trans. Medical Imaging, Vol. 21, No. 1, 2002:1-8, published by Fatemi M, et al., discloses a transducer which is a spherical double-ring array element, wherein the method mainly refers to a small difference frequency which is less than 2% of the base frequency, and focused radiation force generated is used for detecting imaging incentives; the imaging method is known as acoustic vibration imaging.

SUMMARY OF THE PRESENT INVENTION

An object of the present invention is to provide a focused ultrasound split-foci control using spherical-confocal-split array with dual frequency of fundamental and harmonic superimposition, so as to overcome conventional problems such as a low efficiency of single frequency with single-focus, and complex phased array driving control of hundred array elements.

Accordingly, in order to accomplish the above object, the present invention provides:

a spherical-confocal-split array with dual frequency of fundamental and harmonic superimposition, comprising: array elements which are spherically confocal, whose quantity is an even number, wherein a half of the array elements operate with a lower frequency, and the other half of the array elements operate with a higher frequency; both the lower frequency and the higher frequency are MHz high-frequencies; each of the array elements corresponds to a frequency drive; each of array element beams only superimposes inside a focal region instead of outside the focal region; each of the array elements is connected to a channel amplifier through corresponding impedance matching; and a multi-channel waveform controller is connected to the channel amplifier for controlling amplitudes and phases of all channels.

Preferably, a range of the MHz high-frequencies is 1 MHz-10 MHz.

Preferably, a ratio of the higher frequency and the lower frequency is a positive integer.

Preferably, the quantity of the array elements is 2-12.

Preferably, the array elements, which are spherically confocal, are in a spherical sector form, a spherical rectangle form, a spherical ring form, or a spherical vortex form.

Preferably, a method for controlling amplitude phases of the array elements comprises steps of:

defining an array element width as $\Delta w$, defining an array element height as $\Delta h$, and defining an array element area as $\Delta A$; setting an origin of an xyz coordinate at a top point of a spherical cap with a wave beam direction along a z-axis; reckoning a sound pressure $p_m$ of an m-th array element with Reyleigh-Sommerfeld integral, which is calculated with an equation obtained by superimposing N rectangles:

$$p_m = \frac{j\rho ck}{2\pi} u_m \sum_{n=1}^{N} \frac{F_n \Delta A}{R_n} e^{-(\alpha+jk)R_n} \text{sinc} \frac{kx_{sn}\Delta w}{2R} \text{sinc} \frac{ky_{sn}\Delta h}{2R}. \quad (1)$$

wherein each array element m is divided into N sufficiently small squares with same projected areas, then sound pressures at all points of a focal plane are calculated by the equation (1);

wherein in the equation (1), $P_m$ (x, y, z) is a complex sound pressure, $j=\sqrt{-1}$, $\rho$ and c are respectively a media density and a sound velocity, $k=\omega/c$ is a wave number, $u_m$ is a surface particle velocity of the m-th array element, which is used as an array element driving signal; wherein parameter calculation are as follows:

parameters are:

$$R_n = \sqrt{(z-z_n)^2 + (y-y_n)^2 + (x-x_n)^2} \quad (2)$$

$$R = \sqrt{z^2 + (y-y_n)^2 + (x-x_n)^2} \quad (3)$$

$$R_{PP}^2 = R_{SP}^2 - (x_n^2 - y_n^2) \quad (4)$$

$$R_n = R + \frac{1}{R}(R_{SP}^2 - zR_{SP} + z)R_{PP} - \frac{x_n^2 + y_n^2}{2} \quad (5)$$

$$x_{sn} = x - \frac{z - R_{SP}}{R_{PP}} x_n \quad (6)$$

$$y_{sn} = y - \frac{z - R_{SP}}{R_{PP}} y_n. \quad (7)$$

Preferably, a negative peak value at the focal region of the spherical-confocal-split array with dual frequency of fundamental and harmonic superimposition is higher than a cavitation threshold.

A spherical-confocal-split array with dual frequency of fundamental and harmonic superimposition comprises steps of: using spherical sector array elements or spherical rectangle array elements as array elements which are spherically confocal; controlling dual frequencies and phases for generating focal plane split multi-foci which extend a size of a radial focal region, so as to have a larger focal region than with a single-focus; wherein under dual double-frequencies, a sound pressure at the focal region is controlled to be higher than a cavitation threshold; the phase difference of low-frequency and high-frequency of adjacent array elements is 135°; peak-negative pressures of two frequencies encounter at focus, superimposed negative peak values at focus are highest, more cavitation is generated and cavitation activity is strengthened; opposite phase drive of the adjacent array elements provides cavitation clouds strong interference at adjacent foci.

The focused ultrasound split-foci control using spherical-confocal-split array with dual frequency of fundamental and harmonic superimposition comprises steps of: using spherical ring array elements as array elements which are spherically confocal; by applying dual frequencies of second-harmonic superimposition, and controlling a ratio of a high-frequency sound power and a low-frequency sound power, the superimposition of two frequency pressures results in split foci along beam axial within confocal region, wherein the maximal peak intensity of split foci is larger than the sum of two frequency intensities; or applying dual frequencies of third-harmonic superimposition, and controlling the ratio of the high-frequency sound power and the low-frequency sound power; when a phase shift is 60°, obtaining maximum superimposed wave positive peak values and negative peak values.

Compared with conventional technologies, the present invention has advantages as follows.

According to the present invention, the dual-frequency spherical sectorial split array is able to not only generate split multi-foci of the focal plane with the dual frequencies, thereby expanding a volume of a treatment focal region; but also control strong interference of transient cavitation clouds at the adjacent foci, so as to obtain sufficient cavitation-transferred thermal efficiency. The present invention is also able to control the dual-frequency spherical ring array. By controlling sound power amplitude ratio of the dual frequencies, high sound intensity peak values of focal region split foci on an acoustic axis are formed by the focal sound strong interference, which is conducive to cavitation enhancement. With the phase shift of 60°, spherical ring array with dual frequency of third-harmonic superimposition provides an optimized confocal region cavitation heating efficiency.

The present invention is intended to design dual-frequency spherical sectorial array elements and spherical rectangular array elements, and provide the split foci wherein the dual frequencies correspondingly act, which means increases the volume of the focal region while enhances focal region transient cavitation, so as to significantly improve the efficiency of HIFU treatment. By phase control, focal region cavitation is increased and interference is generated between transient cavitation clouds, so as to increase heat production efficiency. The present invention is intended to design the spherical ring array, wherein by simply adjusting dual-frequency drive sound power amplitude ratio, axial split foci within the focal region are obtained and focal sound intensity peak values are maximized (the peak value of sound intensity of split foci produced by the superimposition of dual frequencies is larger than the sum of two frequency intensities, and is nearly twice of the sum). By phase control, interference is generated between transient cavitation clouds, so as to increase heat production efficiency. Spherical vortex array is designed for simultaneously generating focal plane and axial split foci.

BRIEF DESCRIPTION OF THE DRAWINGS

FIGS. 1($b$) and 1($c$) are respectively a focal plane sound intensity view and a focal plane sound intensity contour map of focal plane split foci generated by the spherical sectorial split array of FIG. 1($a$).

FIG. 7($a$) is a focal plane sound intensity map of 4 split foci generated by the dual double-frequencies with a spherical 4-sector split array under a 180° phase shift control; and FIG. 7($b$) is a focal plane sound intensity contour map.

FIG. 8 illustrates waveforms and a superimposed waveform of dual frequency of second-harmonic superimposition with 135° phase difference.

FIG. 9($a$) is a focal plane sound intensity map of 2 split foci generated by the dual frequency of second-harmonic superimposition with the spherical 4-sector split array under a 135° phase shift control; and FIG. 9($b$) is a focal plane sound intensity contour map.

FIG. 10 illustrates axial sound intensity distribution generated by the dual frequency of second-harmonic superimposition with a spherical 2-ring array, wherein a driving power ratio between $f_2$ and $f_1$ is 0.4; strong interference of two frequency waves in the focal region generates about 9 axial split foci, and superimposed sound intensity peak value is about two times of the sum of these two frequency sound intensities.

FIG. 11($b$) is x-z sound intensity contour map, and the strong interference of two frequency waves in the focal region generates about 9 axial split foci.

FIG. 12($b$) illustrates waveforms and a superimposed waveform of dual frequency of third-harmonic superimposition with 0° phase difference.

FIG. 14($b$) is x-z sound intensity contour map, and the strong interference of two frequency waves in the focal region generates about 13 axial split foci.

DETAILED DESCRIPTION OF THE PREFERRED EMBODIMENT

Referring to FIGS. 1(a)-5, the present invention provides a spherical-confocal-split array with dual frequency of fundamental and harmonic superimposition, comprising: array elements which are spherically confocal, whose quantity is an even number (2-12), wherein a half of the array elements operate with a lower frequency, and the other half of the array elements operate with a higher frequency; both the lower frequency and the higher frequency are MHz high-frequencies (1 MHz-10 MHz); each of the array elements corresponds to a frequency drive; each of array element beams only superimposes inside a focal region instead of outside the focal region; each of the array elements is connected to a channel amplifier 3 through corresponding impedance matching 2; and a multi-channel waveform controller 4 is connected to the channel amplifier 3 for controlling amplitudes and phases of all channels.

Figure 1A:
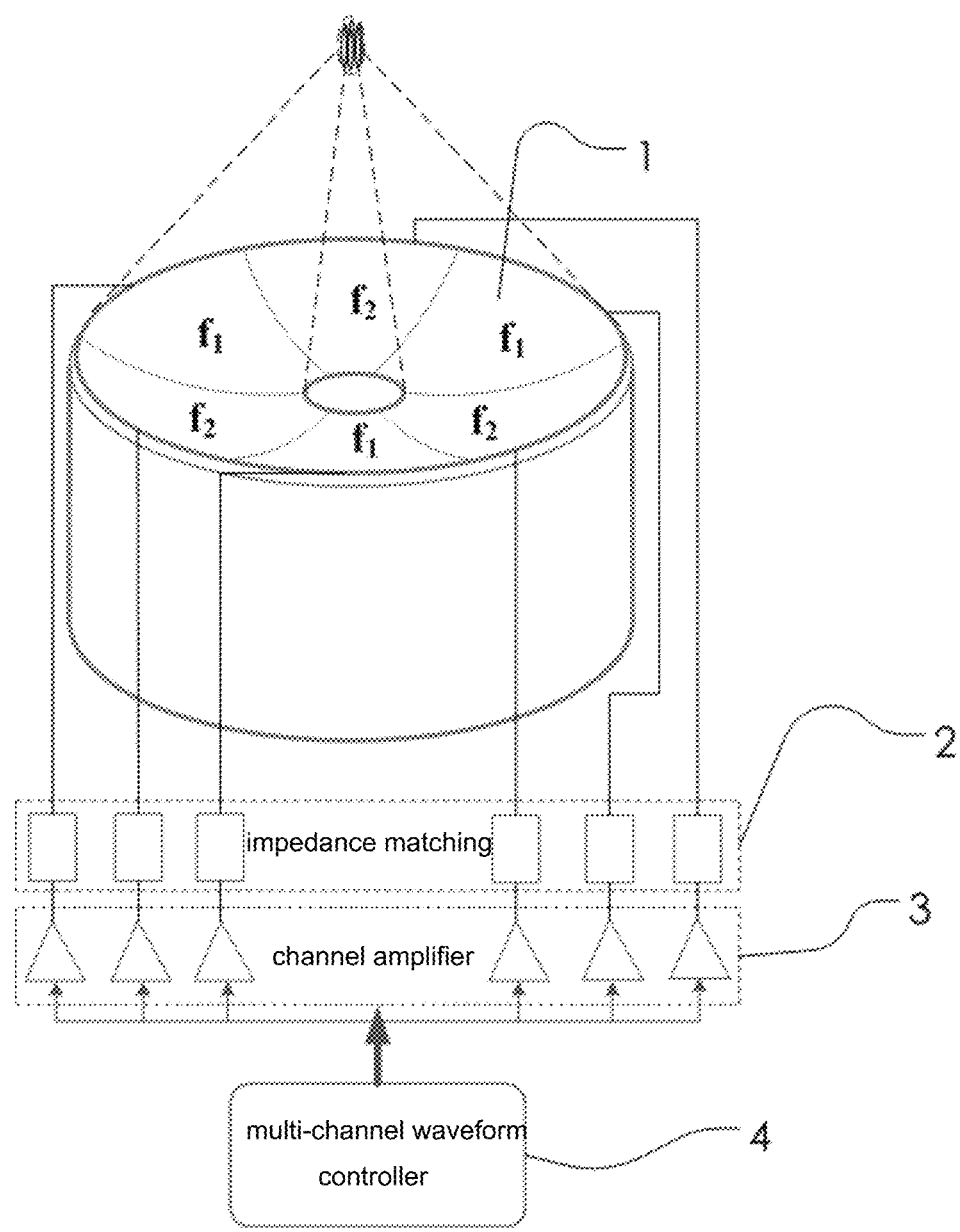
FIG. 1($a$) is a sketch view of a dual-frequency confocal spherical sectorial split array and a system thereof.
Figure 2A:
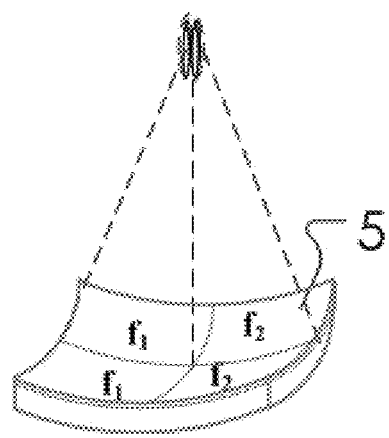
FIGS. 2($a$) and 2($b$) are sketch views of dual-frequency confocal spherical rectangle split arrays with different array element frequency distributions.
Figure 2B:
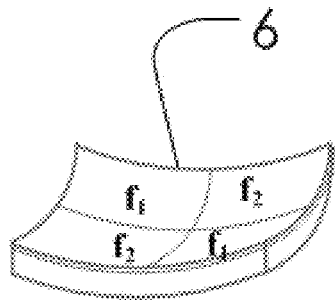
Figure 3:
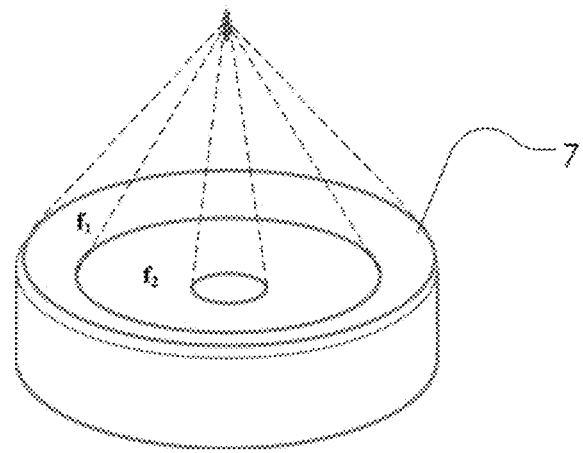
FIG. 3 is a sketch view of a dual-frequency confocal spherical ring array.
Figure 4A:
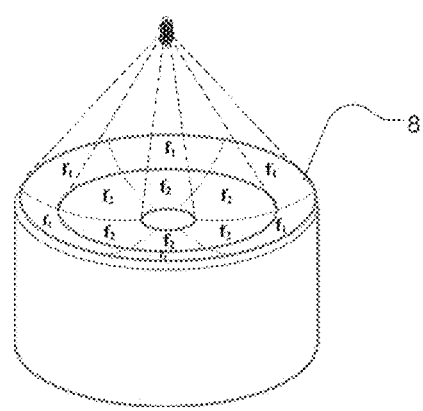
FIGS. 4($a$) and 4($b$) are sketch views of dual-frequency confocal spherical vortex split arrays with different array element frequency distributions.
Figure 4B:
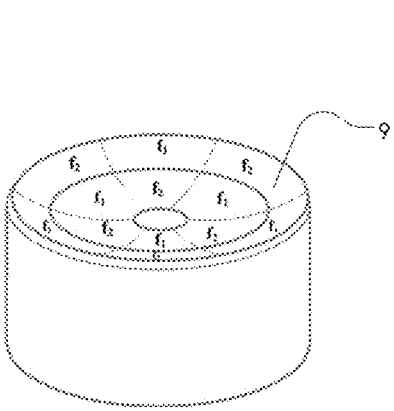

The array elements, which are spherically confocal, may be a spherical sector array 1 (shown in FIG. 1(a)), a spherical rectangle array 5 or 6 (shown in FIGS. 2(a) and 2(b)), a spherical ring array 7 (shown in FIG. 3), or a spherical vortex array 8 or 9 (shown in FIGS. 4(a) and 4(b)).

A method for controlling amplitude phases of the array elements comprises steps of:

defining an array element width as $\Delta w$, defining an array element height as $\Delta h$, and defining an array element area as $\Delta A$; setting an origin of an xyz coordinate at a top point of a spherical cap with a wave beam direction along a z-axis; reckoning a spherical rectangle sound pressure $p_m$ of an m-th array element by:

$$p_m = \frac{j\rho ck}{2\pi} u_m \sum_{n=1}^{N} \frac{F_n \Delta A}{R_n} e^{-(\alpha+jk)R_n} \operatorname{sinc} \frac{kx_{sn}\Delta w}{2R} \operatorname{sinc} \frac{ky_{sn}\Delta h}{2R}. \quad (1)$$

wherein each array element m is divided into N sufficiently small squares with same projected areas, then sound pressures at all points of a focal plane are calculated by the equation (1);

wherein in the equation (1), $P_m$ (x, y, z) is a complex sound pressure, $j=\sqrt{-1}$, $\rho$ and $C$ are respectively a media density and a sound velocity, $k=\omega/c$ is a wave number, $u_m$ is a surface particle velocity of the m-th array element, which is used as an array element driving signal; wherein parameter calculation are as follows:

parameters are:

$$R_n = \sqrt{(z-z_n)^2 + (y-y_n)^2 + (x-x_n)^2} \quad (2)$$

$$R = \sqrt{z^2 + (y-y_n)^2 + (x-x_n)^2} \quad (3)$$

$$R_{PP}^2 = R_{SP}^2 - (x_n^2 + y_n^2) \quad (4)$$

$$R_n = R + \frac{1}{R}\left(R_{SP}^2 - zR_{SP} + z\right)R_{PP} - \frac{x_n^2 + y_n^2}{2}\right) \quad (5)$$

$$x_{sn} = x - \frac{z - R_{SP}}{R_{PP}} x_n \quad (6)$$

$$y_{sn} = y - \frac{z - R_{SP}}{R_{PP}} y_n. \quad (7)$$

The focused ultrasound split-foci control using spherical-confocal-split array with dual frequency of fundamental and harmonic superimposition is specifically described as follows.

1) For the spherical sector array 1: the quantity of the array elements is an even number (2-12), the dual frequencies are MHz high-frequencies (1 MHz-10 MHz); frequencies of all the array elements are shown in FIG. 1(a), wherein the array elements with different frequencies are arranged alternatively, or $f_2$ array elements are arranged on one side (left side) and $f_1$ array elements are arranged on the other side; $f_2/f_1=n$, n=2,3 ... integer.

Figure 6:
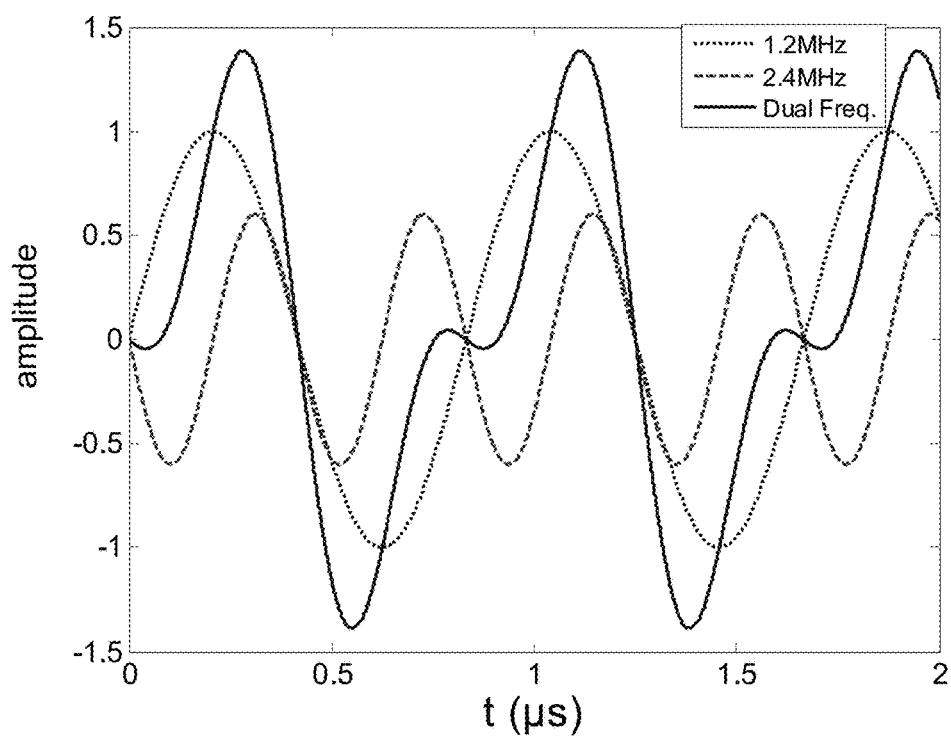
FIG. 6 illustrates waveforms and a superimposed waveform of dual frequency of second-harmonic superimposition with inverted phases (180°).

Referring to FIG. 1(a), 6 array elements are provided. With dual frequencies and phase control, the 6 array elements provide 6 split foci on the focal plane. Therefore, radial distribution of multi-focus is expanded, so as to be 8 times than single-focus during treatment.

Figure 1B:
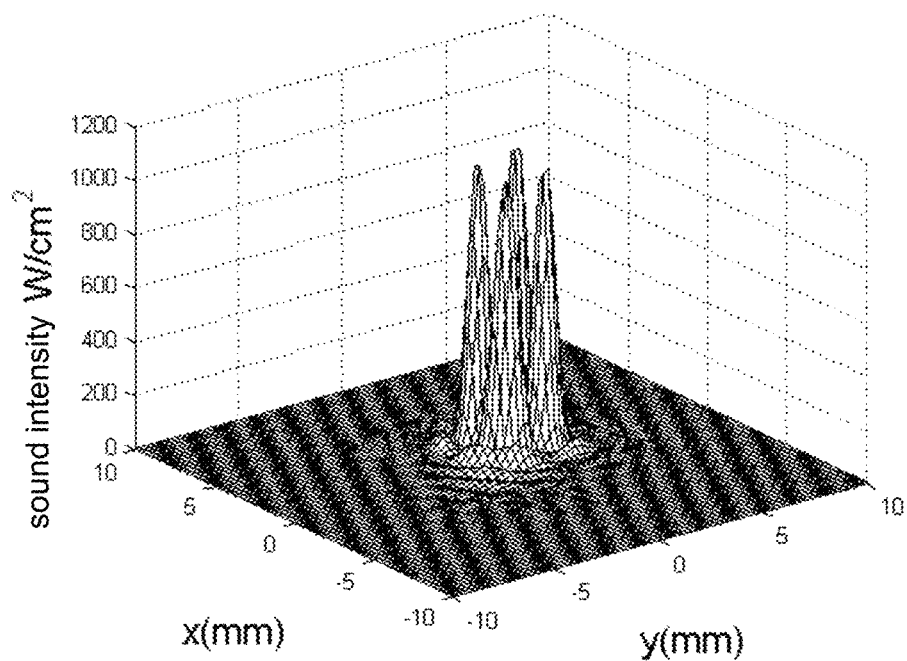

Generally, a focal region sound pressure negative peak value is set to be higher than a cavitation threshold, which can be concluded from FIG. 1(b) which illustrates calculation simulation of the equation (1). Under a dual frequency of second-harmonic superimposition condition, if adjacent array elements are inversely controlled, then peak points of adjacent foci on the focal plane inversely vibrate, and the distance between the adjacent foci is one wavelength of fundamental frequency; if cavitation clouds are located at these two foci, a positive peak cavitation is closed (collapsed) at one focus, and a negative peak is maximally expanded, wherein wideband signals launched by cavitation whose previous vibration period is closed (collapsed) will reach such maximum cavitation, so a thermal absorption efficiency is highest, which is a cavitation strong interference.

Effects of ultrasonic cavitation, especially transient cavitation (or inertial cavitation), enable a thermal ablation to be at least 6 times higher than the one without cavitation. The present invention takes full advantage of such ultrasonic cavitation mechanism for providing high-efficiency precise treatment. Firstly, the present invention provides simultaneous superimposition of confocal dual-frequency ultrasound in the focal region, wherein the dual frequencies are both MHz high-frequencies with an integral-multiple relationship, such as 1 MHz and 2 MHz, or 1 MHz and 3 MHz. The dual-frequency is suitable for a continuous wave or a pulse wave with a string length of more than 10 wave numbers. Dual-frequency wave superposition in the focal region will lower the cavitation threshold, wherein the cavitation threshold is lower than that of a low-frequency wave, while the transient cavitation and cavitation thermal absorption are strengthened. Referring to the dual frequency of second-harmonic superimposition in FIG. 6, each low-frequency periodic wave peak superposition increases, and the negative peak value also increases. Meanwhile, velocity is faster and increase of the negative peak will generate more cavitation. Spherical array elements are able to provide confocal control. Each of the array elements only superimposes inside the focal region instead of outside the focal region. Therefore, array element transducers with compact distribution of spherical sector, rectangle, ring and vortex array elements are used. With a single frequency, the spherical sector array will generate separated annular array multi-foci, and each array element corresponds to one focus, namely the split focus and the split array. Focal region volume expansion is equal with such multi-foci and multi-foci generated by a phased array comprising 128 or 256 array elements, but only by controlling the phases of a few spherical sector arrays, the focal region volume will be expanded by the split foci.

2) For the spherical rectangle array 5 or 6: referring to FIGS. 2(*a*) and 2(*b*), all characteristics and control thereof are the same as that of the spherical sector array.

3) For the spherical ring array 7: referring to FIG. 3, the quantity of the array elements is 2; under a certain ratio of sound power amplitudes of the dual frequencies, a plurality of the split foci are generated along the acoustic axis in the focal region; and dual-frequency superimposed sound intensity peak value is nearly two times of a sum of these two frequency sound intensities, which indicates strong interference of dual-frequency sonic wave.

A precise axial sound pressure equation of a sound pressure of the spherical ring array 7 along the acoustic axis is able to be obtained by Reyleigh-Sommerfeld integral, so as to obtain a precise sound pressure equation, wherein axial sound pressure equation of each ring is:

$$P(z) = \begin{cases} j\rho c k R_{SR} u \dfrac{e^{-(\alpha+jk)\sqrt{\left(z-R_{SR}+\sqrt{R_{SR}^2-R_2^2}\right)^2+R_2^2}} - e^{-(\alpha+jk)\sqrt{\left(z-R_{SR}+\sqrt{R_{SR}^2-R_1^2}\right)^2+R_1^2}}}{(z-R_{SR})(\alpha+jk)} & \text{if } z \neq R_{SR} \\ j\rho c k u\left(\sqrt{R_{SR}^2-R_1^2}-\sqrt{R_{SR}^2-R_2^2}\right)e^{-(\alpha+jk)R_{SR}} & \text{if } z = R_{SR} \end{cases} \quad (2)$$

wherein a wave number:

$$k = \frac{\omega}{c} = \frac{2\pi f}{c};$$

$\alpha$ is an attenuation coefficient; $R_{SR}$ is a radius of curvature of each ring; $R_1$ is a radius of an inner hole of each ring, $R_2$ is a radius of an outer ring of each ring; and u is an array element surface vibration velocity which is proportional to an array element driving sound pressure.

Sound pressure calculation of two frequency rings is: firstly using the equation (2) to calculate the sound pressure of each frequency ring, and then adding to obtain axially sound pressure of the spherical ring array 7.

With a certain frequency amplitude ratio, strong cavitation interference at a plurality of the foci is able to be obtained under two frequency phases.

4) For spherical vortex array 8 or 9: referring to FIGS. 4(*a*) and 4(*b*), the quantity of the array elements is an even number (4, 8 or 12); all control methods are the same as that of the spherical sector array 1; like the spherical sector array elements, split multi-foci on focal plane are generated for expanding the focal region treatment volume, and sound power ratio of the dual frequencies is adjustable for obtaining axial high sound intensity of the split foci.

Figure 1C:
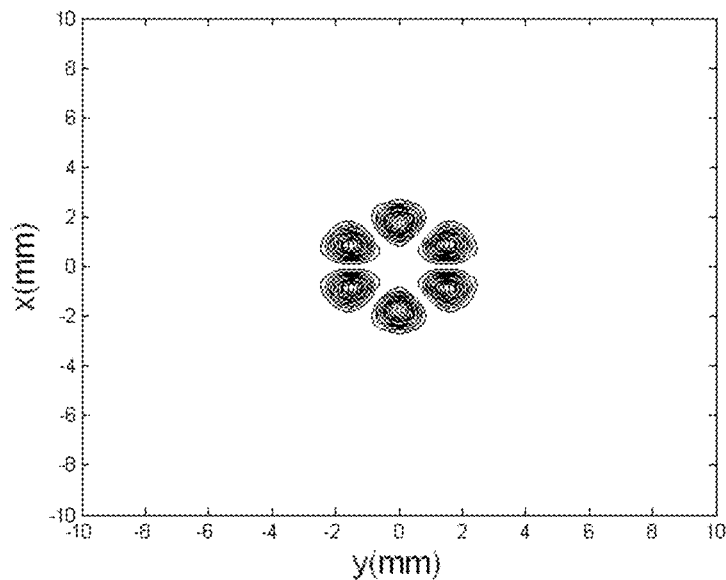

Driving controls of the spherical rectangle, ring and vortex arrays have a same structure as the driving control of the spherical sector array as shown in FIG. 1(*a*).

Figure 5:
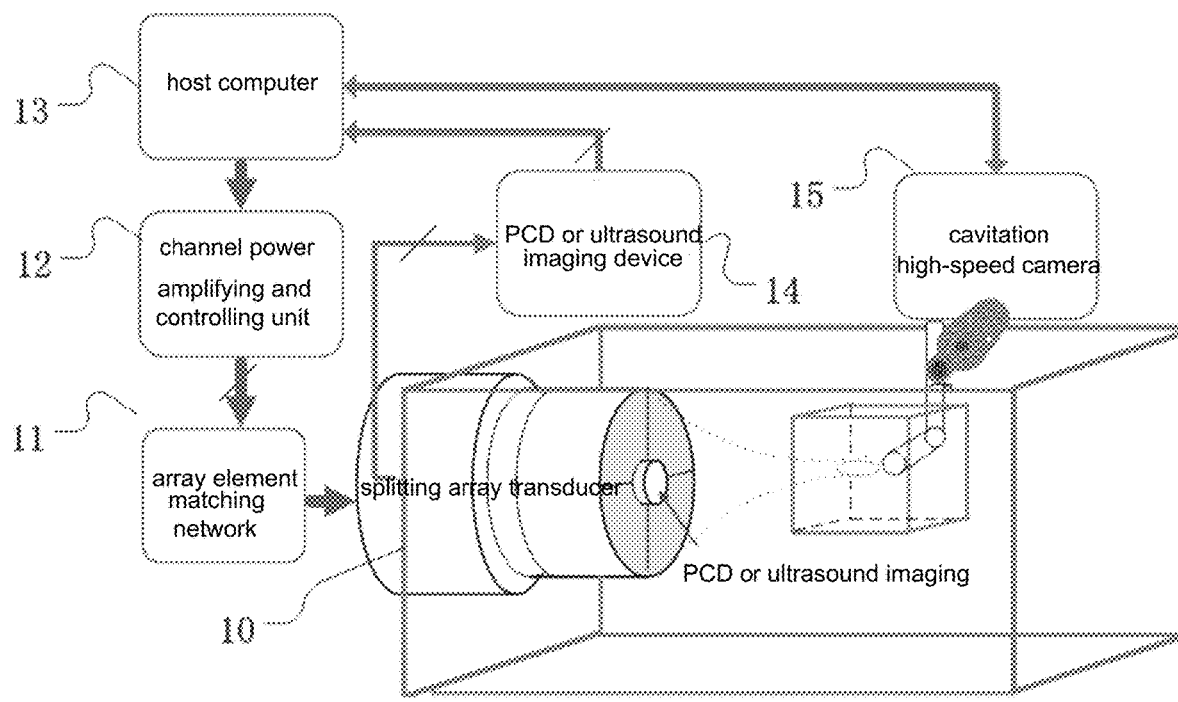
FIG. 5 is sketch view of a system for controlling and detecting focal region cavitation mechanism enhanced by the dual-frequency confocal split array.

An experimental system according to preferred embodiments of dual-frequency split focus modes of the above split arrays are shown in FIG. 5, wherein HIFU focus mode ultrasonic cavitation in transparent tissue phantom contained bovine albumin (BSA) may be estimated by a cavitation high-speed camera 15, and a PCD or ultrasound imaging device 14; a host computer 13 is responsible for controlling the split focus modes, the cavitation high-speed camera 15 and the PCD (passive cavitation detection) 14; the host computer 13 sends phase and amplitude information of a dual-frequency split focus mode to a channel power amplifying and control unit 12 which generates waveforms needed by each array element and sends to a split array transducer 10 through as array element matching network 11; the split array transducer 10 sends the split focus modes.

According to a preferred embodiment 1, the split array is the spherical 4-sector array (see element 1, FIG. 1(*a*)), wherein the dual frequencies of second-harmonic superimposition are $f_1=1.2$ MHz and $f_2=2.4$ MHz, and frequency distribution of the array elements are $f_2$ array elements on one side (left side) and $f_1$ array elements on the other side (see element 5, FIG. 2(*a*)). FIG. 6 illustrates waveforms and a superimposed waveform of the dual frequency of second-harmonic superimposition with inverted phases (180°), wherein after superposition, the positive peak value increases, and the negative peak value also increases. Meanwhile, the velocity is faster and increase of the negative peak will generate more cavitation. FIGS. 7(*a*) and 7(*b*) illustrate the sound intensity distribution of the 4 split foci generated by the adjacent array elements with opposite phases, which proves that dual frequencies of second-harmonic superimposition are also able to produce 4 split foci, while such control ensures that the focal region sound pressure is higher than the cavitation threshold. The adjacent foci on the focal plane inversely vibrate, and the distance between the adjacent foci is one wavelength of fundamental frequency; cavitation cloud strong interference at the adjacent foci is generated under a transient cavitation condition, so as to obtain efficient transient cavitation thermal conversion results. For the same spherical 4-sector array, if adjacent same frequency array elements have equal phases (0°), and adjacent array elements with dual frequency of second-harmonic superimposition have a low-frequency phase difference of 135°, waveforms and a superimposed waveform of dual frequency of second-harmonic superimposition with 135° phase difference is shown in FIG. 8, wherein after superimposition, the positive wave is widened while its peak value doesn't increase, and two negative peaks superimpose to provide a maximum superimposed negative peak value, which is most conducive to generating more cavitation. FIGS. 9(*a*) and 9(*b*) illustrate the sound intensity distribution of the 2 split foci whose adjacent same frequency array elements have equal phases (0°), and adjacent array elements with dual frequency of second-harmonic superimposition have a phase difference of 135°.

Figure 11A:
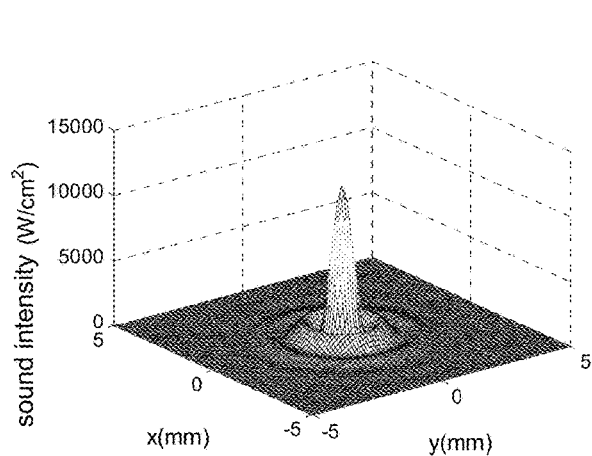
FIG. 11($a$) illustrates axial sound intensities generated by the dual frequency of second-harmonic superimposition with the spherical 2-ring array, wherein the driving power ratio between $f_2$ and $f_1$ is 0.4.
Figure 11B:
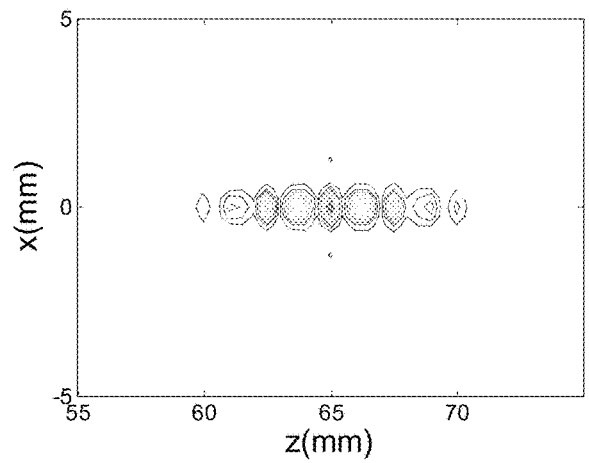

According to a preferred embodiment 2, the split array is the spherical 2-ring array (see element 7, FIG. 3), wherein the dual frequencies of second-harmonic superimposition are $f_1=1.1$ MHz and $f_2=2.2$ MHz. As a result, there is no focal plane radially split focus, and a confocal superposition result is only focal region superimposition. With the precise axial sound pressure equation (2), axial sound pressure superimposed results are obtained, as shown in FIG. 10. Due to sufficient dual-frequency focal region coverage, strong interference is generated by two waves at the focal region, resulting in about seven split foci in the focal region superimposed results, and the distance between the adjacent foci is one wavelength of fundamental frequency. The split foci generated depend on the ratio of the high-frequency and low frequency sound power instead of the dual-frequency phases. When the ration is $APf_2/APf_1=0.4$, then strong interference is generated by two waves. At this time, the peak value of sound intensity of split foci produced by the superimposition of dual frequency is larger than the sum of two frequency intensities, and is nearly twice of the sum. The results of waveform superimposition of this dual frequency of second-harmonic superimposition are similar to those of the sector array which are shown in FIGS. 6 and 8, which means when the phase shift is 135°, the negative peak superimposition is maximized and cavitation generation is best. When the phase shift is 135°, the adjacent foci inversely vibrate, and cavitation cloud strong interference at the two foci is generated under a transient cavitation condition. FIGS. 11(a) and 11(b) illustrate focus sound intensity distribution of the spherical 2-ring array, wherein FIG. 11(a) illustrates the focus sound intensity distribution on the focal plane, wherein sound power control based on such array elements ensures that the focal region sound pressure is higher than the cavitation threshold during experiment; and FIG. 11(b) illustrates 7 axial split foci.

Figure 12A:
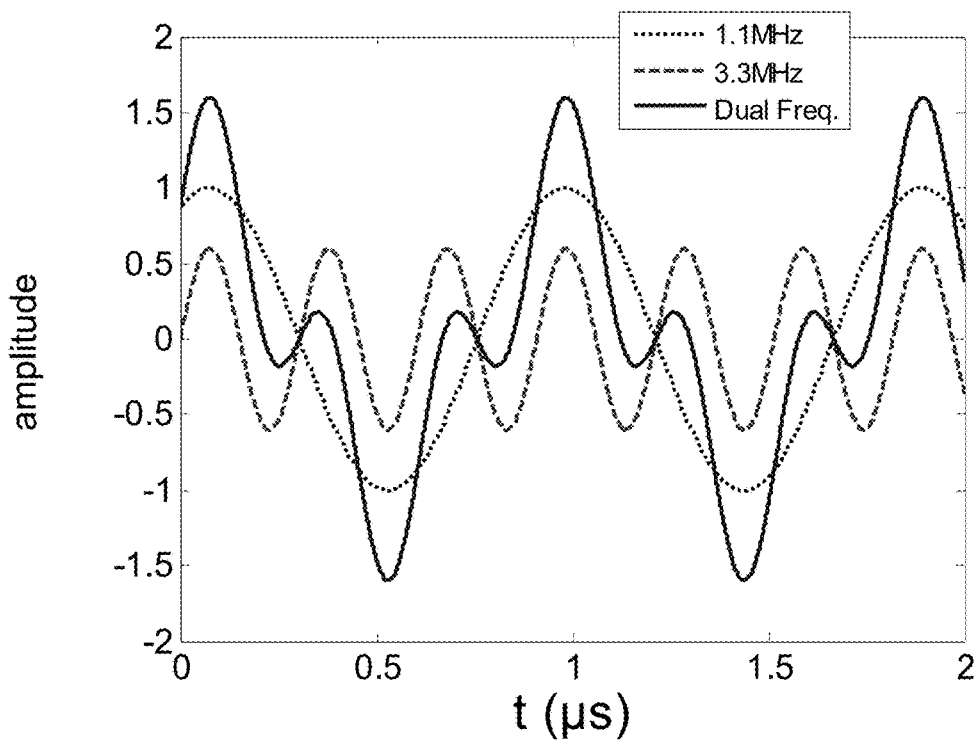
FIG. 12($a$) illustrates waveforms and a superimposed waveform of dual frequency of third-harmonic superimposition with 60° phase difference.
Figure 12B:
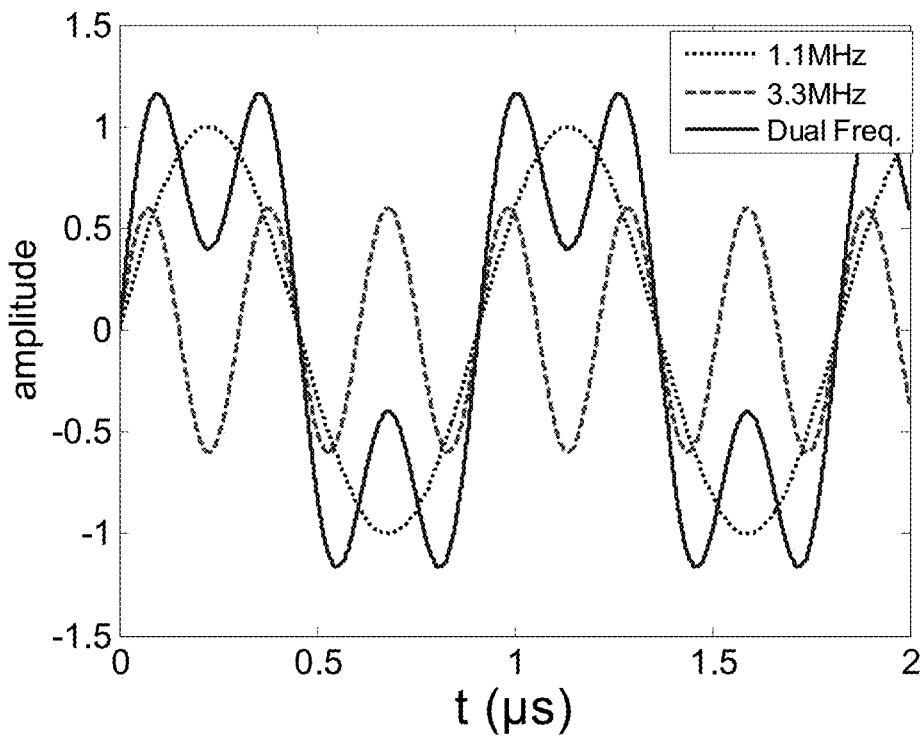
Figure 13:
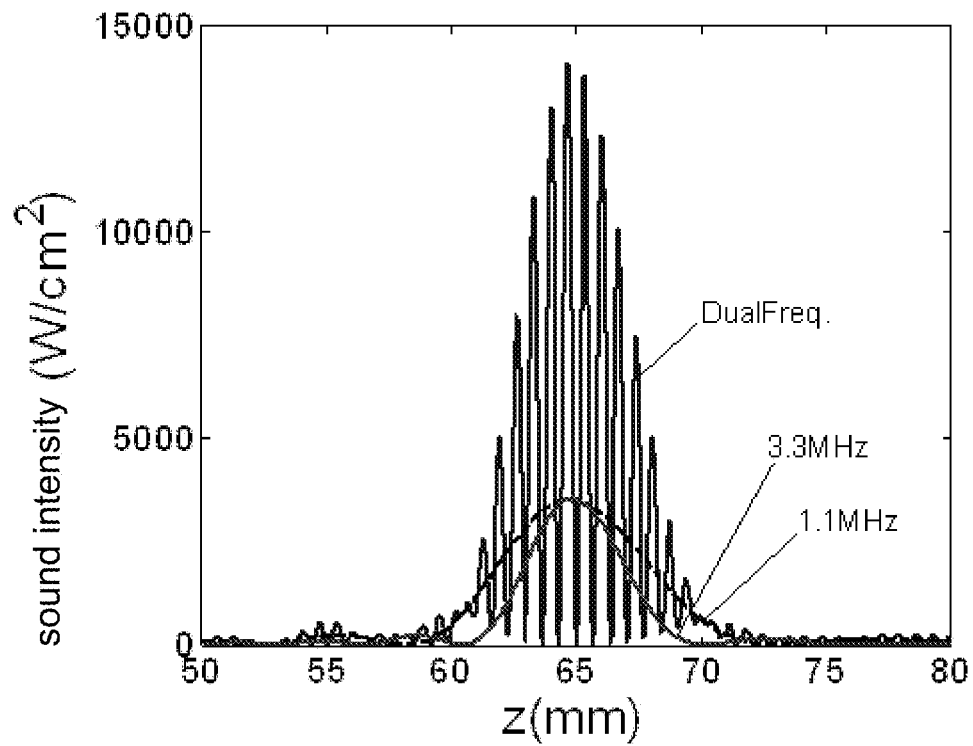
FIG. 13 illustrates axial sound intensity distribution generated by the dual frequency of third-harmonic superimposition with a spherical 2-ring array, wherein a driving power ratio between $f_2$ and $f_1$ is 0.28; strong interference of two frequency waves in the focal region generates about 13 axial split foci, and superimposed sound intensity peak value is about two times of the sum of these two frequency sound intensities.
Figure 14A:
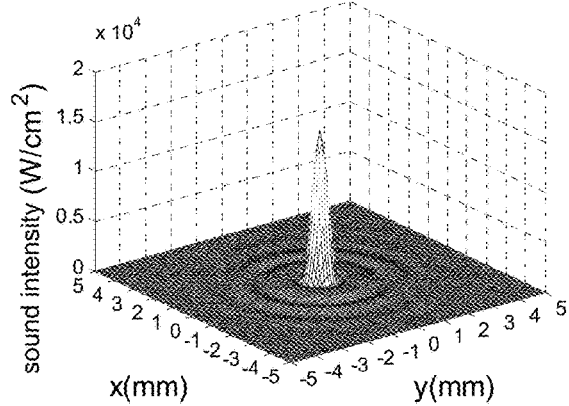
FIG. 14($a$) illustrates axial sound intensities generated by the dual frequency of third-harmonic superimposition with the spherical 2-ring array, wherein the driving power ratio between $f_2$ and $f_1$ is 0.28.
Figure 14B:
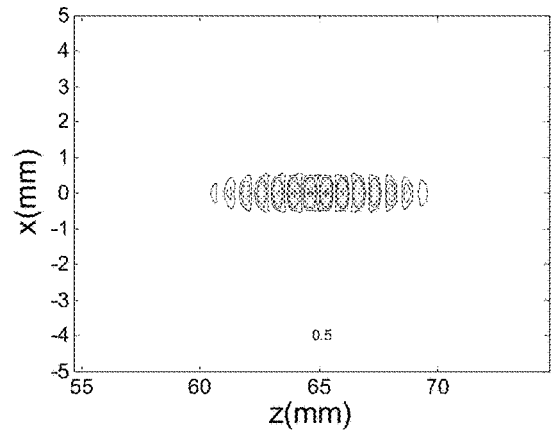

According to a preferred embodiment 3, the split array is the spherical 2-ring array (see element 7, FIG. 3), wherein the dual frequencies of third-harmonic superimposition are $f_1=1.1$ MHz and $f_2=3.3$ MHz. When it comes to waveform superimposition, one phase superposition of the dual frequency of third-harmonic superimposition is most conducive to cavitation efficiency, wherein when a low-frequency wave phase is 60°, two positive peaks encounter as well as two negative peaks, so both are maximized, which is conducive to cavitation generation and collapse, see FIG. 12(a); when the low-frequency wave phase is 0°, the positive and negative peaks encounter, so peak values are minimized, see 12(b). FIG. 13 shows when the ration is $APf_2/APf_1=0.4$, then strong interference is generated by the two waves, about 13 split foci are generated due to superimposition, and the distance between the adjacent foci is a half wavelength of fundamental frequency. FIGS. 14(a) and 14(b) illustrate focus sound intensity distribution of the spherical 2-ring array with dual frequency of third-harmonic superimposition, wherein FIG. 14(a) illustrates the focus sound intensity distribution on the focal plane, wherein sound power control based on such array elements ensures that the focal region sound pressure is higher than the cavitation threshold during experiment; and FIG. 14(b) illustrates 13 axial split foci.

Figure 15:
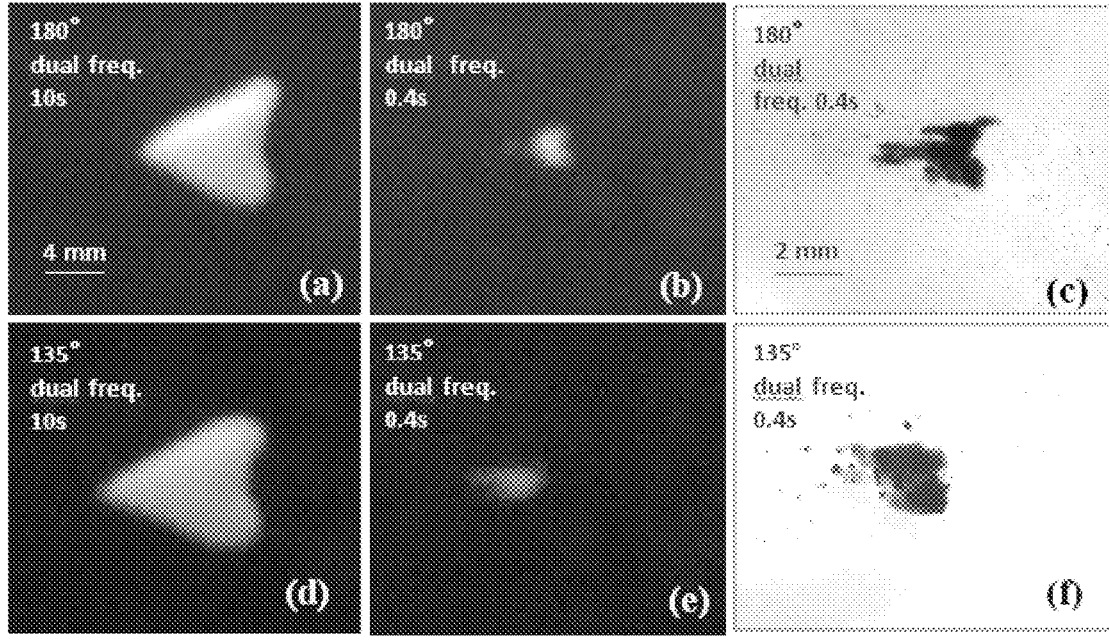
FIG. 15 illustrates focal injury experimental results in a transparent phantoms (polyacrylamide gel coined bovine albumin, BSA), caused by the dual frequency of second-harmonic superimposition with the spherical 4-sector split array under 180° and 135° phase shift control, which is obtained by videos, high-speed photography and PCD (passive cavitation detection) (see FIG. 16); wherein, (a), (b) and (c) are results of the 180° phase shift control; (a) and (b) are video images, and (c) is a high-speed photography image; (d), (e) and (f) are results of the 135° phase shift control; (d) and (e) are video images, and (f) is a high-speed photography image.
Figure 16:
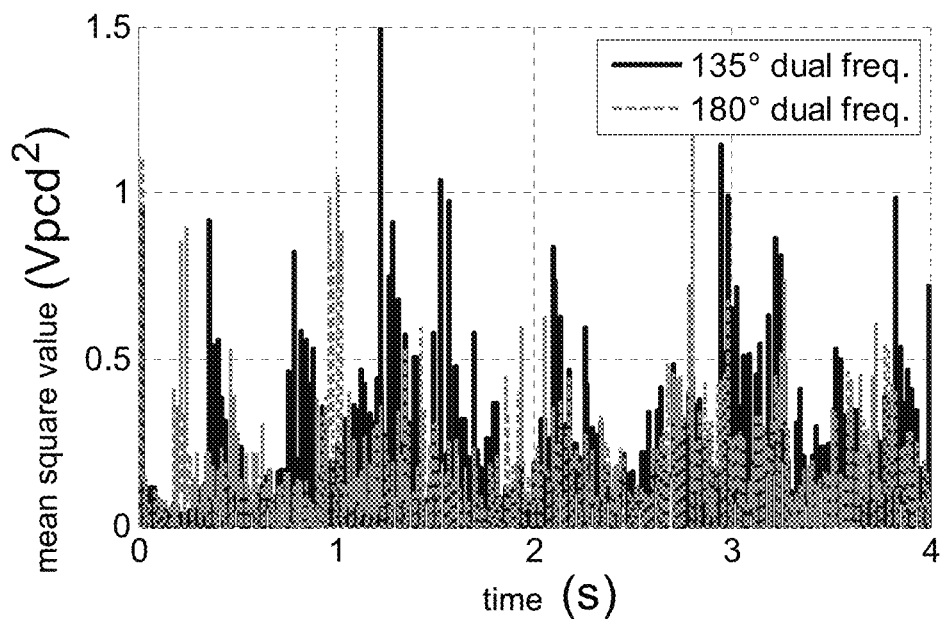
FIG. 16 illustrates focal injury PCD results in the transparent phantoms (polyacrylamide gel coined bovine albumin, BSA), caused by the dual frequency of second-harmonic superimposition with the spherical 4-sector split array under 180° and 135° phase shift control, wherein after comb-like filter, a mean square value of wideband signals with harmonic filtered reflects focal region transient cavitation (inertial cavitation) energy.

According to the preferred embodiment 1, experimental results of the dual frequency of second-harmonic superimposition with the spherical 4-sector split array under 180° and 135° phase shift control are shown in FIG. 15 which illustrates two best split focus modes. In the 180° mode, a shape of the cavitation clouds strong interference at the four foci is shown in FIG. 15(c), wherein cavitation clouds at the four foci rapidly move towards the transducer in parallel, and generate effective thermal ablation as shown in FIG. 15(b). FIGS. 5(c) and 5(b) are similar, indicating effective cavitation thermal ablation. In the 135° mode, there is a large cavitation region at two foci in the focal region, and a shape of the cavitation clouds strong interference is shown in FIG. 15(f), wherein cavitation clouds at the two foci rapidly move towards the transducer in parallel, and generate effective thermal ablation as shown in FIG. 15(e). FIGS. 5(f) and 5(e) are similar, indicating effective cavitation thermal ablation. Although a total sound power of the 135° mode is lower than that of the 180° mode, namely 0.8 times, damage sizes during final 10 s are both about 10 mm×10 mm×11 mm, indicating that the 135° mode produces more cavitation and stronger cavitation effect. The injury experiments with 180° and 135° phase shift control are simultaneously detected by PCD, and results thereof are shown in FIG. 16. After comb-like filter, a mean square value of wideband signals with harmonic filtered reflects focal region transient cavitation (inertial cavitation) energy. Referring to FIG. 16, 135° phased inertial cavitation energy is slightly higher than 180° phased inertial cavitation energy, proving that the 135° mode produce more cavitation and stronger cavitation effect.

Figure 17:
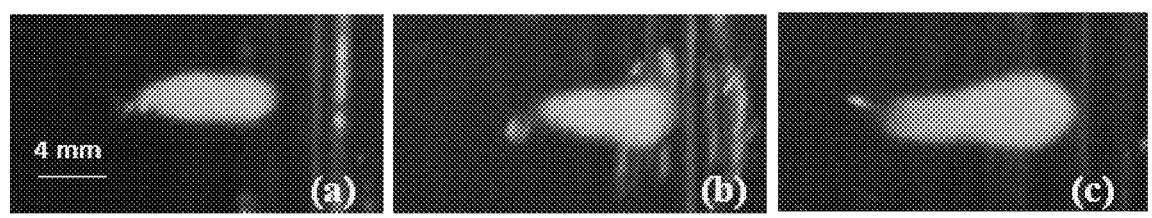
FIG. 17 illustrates focal injury experimental results in the transparent phantoms (polyacrylamide gel coined bovine albumin, BSA), caused by the dual frequency of second-harmonic superimposition with the spherical 2-ring split array, wherein (a) is video results generated by the dual frequency of second-harmonic superimposition with 135° phase shift control and the driving power ratio between $f_2$ and $f_1$ is $APf_2/APf_1=0.371$; and illustrates the dual frequency of third-harmonic superimposition with same structural parameters of the spherical 2-ring array and the driving power ratio between $f_2$ and $f_1$ is $APf_2/APf_1 = 0.28$; (b) is results of 0° phase shift control; and (c) is 60° shift phase control

FIG. 17(a) illustrates experimental results of the spherical 2-ring split array with the dual frequency of second-harmonic superimposition, wherein treatment parameters are: dual frequency of second-harmonic superimposition of $f_1=1.1$ MHz and $f_2=2.2$ MHz, 135° phase shift, a low-frequency sound power of 70 w, a high-frequency sound power of 26 w, and a treatment period of 10 s. A damage size shown is 3 mm×3 mm×8.7 mm, wherein because cavitation damages are caused faster at the split foci on the acoustic axis of the focal region, an overall damage shape is cylindrical, which is suitable for focus arrangement during treatment planing.

With same spherical 2-ring array structural parameters, FIGS. 17(b) and 17(c) illustrate experimental results with dual frequency of third-harmonic superimposition, wherein treatment parameters are: dual frequency of third-harmonic superimposition of $f_1=1.1$ MHz and $f_2=3.3$ MHz, 60° and 0° phases shift, a low-frequency sound power of 70 w, a high-frequency sound power of 20 w, and a treatment period of 10 s. 0° phase shift damage is shown in FIG. 7(b), wherein a damage size is 3.6 mm×3.6 mm×8 mm. 60° phase shift damage is shown in FIG. 7(c), wherein a damage size is 4.4 mm×4.4 mm×10.8 mm. With the dual frequency of third-harmonic superimposition, although a high-frequency sound power is 6 w lower, but the damage size is larger than the one with dual frequency of second-harmonic superimposition, wherein with 0° phase shift, the dual frequency of third-harmonic superimposition damage size is 1.3 times of the dual frequency of second-harmonic superimposition damage size; with 60° phase shift, the triple-frequency damage size is 2.6 times of the dual frequency of second-harmonic superimposition damage size. High-frequency increase and closer split foci may be a reason for damage size increase. The dual frequency of third-harmonic superimposition damage size is largest with 60° phase shift because the superimposition of these two frequencies makes the superimposed positive and negative peak values maximal, thus generating more and stronger cavitation.

What is claimed is:

1. A method of focused ultrasound split-foci control using spherical-confocal-split array with dual frequency of fundamental and harmonic superimposition, which is based on a dual-frequency confocal superimposed focused ultrasonic spherical splitting array, comprising steps of: using spherical sector array elements or spherical rectangle array elements as array elements which are spherically confocal; controlling the array elements to emit dual frequencies at chosen phases for generating focal plane split multi-foci which extend a size of a radial focal region, so as to have a larger focal region than with a single-focus; wherein under dual frequency of second-harmonic superimposition, a sound pressure at the radial focal region is controlled to be higher than a cavitation threshold;

wherein a method for controlling amplitude phases of the array elements comprises steps of:

defining an array element width as $\Delta w$, defining an array element height as $\Delta h$, and defining an array element area as $\Delta A$; setting an origin of an xyz coordinate at a top point of a spherical cap with a wave beam direction along a z-axis; reckoning a sound pressure $p_m$ of an m-th array element with Reyleigh-Sommerfeld integral, which is calculated with an equation obtained by superimposing N rectangles:

$$p_m = \frac{j\rho ck}{2\pi} u_m \sum_{n=1}^{N} \frac{F_n \Delta A}{R_n} e^{-(\alpha+jk)R_n} \text{sinc}\frac{kx_{sn}\Delta w}{2R} \text{sinc}\frac{ky_{sn}\Delta h}{2R}. \quad (1)$$

(1)
wherein each array element m is divided into N squares with same projected areas, then sound pressures at all points of a focal plane are calculated by the equation (1);
wherein in the equation (1), $P_m$ (x, y, z) is a complex sound pressure, $j=\sqrt{-1}$, $\rho$ and C are respectively a media density and a sound velocity, $k=\omega/c$ is a wave number, $u_m$ is a surface particle velocity of the m-th array element, which is used as an array element driving signal; wherein parameter calculation are as follows:
parameters are:

$$R_n = \sqrt{(z-z_n)^2 + (y-y_n)^2 + (x-x_n)^2} \quad (2)$$

$$R = \sqrt{z^2 + (y-y_n)^2 + (x-x_n)^2} \quad (3)$$

$$R_{PP}^2 = R_{SP}^2 - (x_n^2 + y_n^2) \quad (4)$$

$$R_n = R + \frac{1}{R}\left(R_{SP}^2 - zR_{SP} + z\right)R_{PP} - \frac{x_n^2 + y_n^2}{2}\right) \quad (5)$$

$$x_{sn} = x - \frac{z - R_{SP}}{R_{PP}} x_n \quad (6)$$

$$y_{sn} = y - \frac{z - R_{SP}}{R_{PP}} y_n. \quad (7)$$

2. A method of focused ultrasound split-foci control using spherical-confocal-split array with dual frequency of fundamental and harmonic superimposition, which is based on the spherical-confocal-split array with the dual frequency of fundamental and the harmonic superimposition, comprising steps of:
using spherical ring array elements as array elements which are spherically confocal; and
applying dual frequencies, and controlling a ratio of a high-frequency sound power and a low-frequency sound power, wherein the superimposition of two frequency pressures results in split foci along beam axial within confocal region, and the maximal peak intensity of split foci is larger than the sum of two frequency intensities of the high-frequency sound power and the low-frequency sound power; or
applying a dual frequency of third-harmonic superimposition, and controlling the ratio of the high-frequency sound power and the low-frequency sound power; when a phase shift is 60°, obtaining maximum superimposed wave positive peak values and negative peak values;
wherein a method for controlling amplitude phases of the array elements comprises steps of:
defining an array element width as $\Delta w$, defining an array element height as $\Delta h$, and defining an array element area as $\Delta A$; setting an origin of an xyz coordinate at a top point of a spherical cap with a wave beam direction along a z-axis; reckoning a sound pressure $p_m$ of an m-th array element with Reyleigh-Sommerfeld integral, which is calculated with an equation obtained by superimposing N rectangles:

$$p_m = \frac{j\rho ck}{2\pi} u_m \sum_{n=1}^{N} \frac{F_n \Delta A}{R_n} e^{-(\alpha+jk)R_n} \text{sinc}\frac{kx_{sn}\Delta w}{2R} \text{sinc}\frac{ky_{sn}\Delta h}{2R}. \quad (1)$$

wherein each array element m is divided into N squares with same projected areas, then sound pressures at all points of a focal plane are calculated by the equation (1);
wherein in the equation (1), $P_m$ (x, y, z) is a complex sound pressure, $j=\sqrt{-1}$, $\rho$ and C are respectively a media density and a sound velocity, $k=\omega/c$ is a wave number, $u_m$ is a surface particle velocity of the m-th array element, which is used as an array element driving signal; wherein parameter calculation are as follows:
parameters are:

$$R_n = \sqrt{(z-z_n)^2 + (y-y_n)^2 + (x-x_n)^2} \quad (2)$$

$$R = \sqrt{z^2 + (y-y_n)^2 + (x-x_n)^2} \quad (3)$$

$$R_{PP}^2 = R_{SP}^2 - (x_n^2 - y_n^2) \quad (4)$$

$$R_n = R + \frac{1}{R}\left(R_{SP}^2 - zR_{SP} + z\right)R_{PP} - \frac{x_n^2 + y_n^2}{2}\right) \quad (5)$$

$$x_{sn} = x - \frac{z - R_{SP}}{R_{PP}} x_n \quad (6)$$

$$y_{sn} = y - \frac{z - R_{SP}}{R_{PP}} y_n. \quad (7)$$

* * * * *